United States Patent
Müller et al.

(10) Patent No.: US 8,879,809 B2
(45) Date of Patent: Nov. 4, 2014

(54) METHOD TO PROCESS MEDICAL IMAGE DATA

(75) Inventors: Edgar Müller, Heroldsbach (DE); Peter Speier, Erlangen (DE); Michael Zenge, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 120 days.

(21) Appl. No.: 13/569,380

(22) Filed: Aug. 8, 2012

(65) Prior Publication Data

US 2013/0039549 A1     Feb. 14, 2013

(30) Foreign Application Priority Data

Aug. 8, 2011  (DE) .................... 10 2011 080 591

(51) Int. Cl.
| | | |
|---|---|---|
| G06T 7/00 | (2006.01) | |
| G01R 33/54 | (2006.01) | |
| G01R 33/56 | (2006.01) | |
| H04N 19/60 | (2014.01) | |
| G01R 33/561 | (2006.01) | |
| A61B 6/00 | (2006.01) | |

(52) U.S. Cl.
CPC ........ *G01R 33/543* (2013.01); *H04N 19/00775* (2013.01); *G01R 33/5611* (2013.01); *A61B 6/5211* (2013.01); *G01R 33/5608* (2013.01)
USPC ........................................................ 382/128

(58) Field of Classification Search
USPC ........................................................ 382/128
See application file for complete search history.

(56) References Cited

U.S. PATENT DOCUMENTS

| | | | |
|---|---|---|---|
| 2003/0228041 A1* | 12/2003 | Bae et al. ....................... 382/131 |
| 2006/0048114 A1* | 3/2006 | Schmidt ........................ 717/148 |
| 2006/0089541 A1* | 4/2006 | Braun et al. .................. 600/300 |
| 2006/0206874 A1* | 9/2006 | Klein ............................. 717/136 |
| 2010/0217110 A1* | 8/2010 | Hughes et al. ................ 600/410 |
| 2010/0277173 A1 | 11/2010 | Landschuetz et al. |
| 2010/0317962 A1* | 12/2010 | Jenkins et al. ................ 600/411 |
| 2011/0095762 A1 | 4/2011 | Piccini et al. |
| 2011/0153231 A1 | 6/2011 | Greiser et al. |

OTHER PUBLICATIONS

An Introducation to Compressive Sampling. Emmanuel Candes and Michael Wakin. Mar. 2008.*
An Automatch Appraoch to Invariant Radiograph Classification. J. Dahmen, D. Keysers, M. Motter, H. Ney, T. Lehmann, B. Wein. 2001.*
"Sparse MRI: The Application of Compressed Sensing for Rapid MR Imaging," Lustig et al., Magnetic Resonance in Medicine, vol. 58 (2007), pp. 1182-1195.
"Imaging via Compressive Sampling," Romberg, IEEE Signal Processing Magazine, (Mar. 2008), pp. 14-20.

(Continued)

*Primary Examiner* — Stephen R Koziol
*Assistant Examiner* — Delomia Gilliard
(74) *Attorney, Agent, or Firm* — Schiff Hardin LLP

(57) ABSTRACT

A method to process medical image data has the following features. Immediately compressed raw data are acquired by an imaging medical technology apparatus. The compressed raw data are stored. In addition to the compressed raw data, processing data are stored which are provided to generate output data from the compressed raw data, wherein the file size of the compressed raw data and the processing data in total is less than the file size of the output data.

7 Claims, 1 Drawing Sheet

(56) References Cited

OTHER PUBLICATIONS

"An Introduction to Compressive Sampling," Candes et al., IEEE Signal Processing Magazine, (Mar. 2008), pp. 21-30.

Agarwal et al.: "Adaptive Asynchronous Analog to Digital Conversion for Compressed Biomedical Sensing", Biomedical Circuits and Systems Conference, 2009, BioCAS 2009, IEEE, pp. 69-72, Nov. 26-28, 2009, doi: 10.1109/BIOCAS.2009.5372083.

Saltzer, "Technology, Networks, and the Library of the Year 2000", Springer Berlin Heidelberg; Future Tendencies in Computer Science, Control and Applied Mathematics, Lecture Notes in Computer Science, vol. 653, pp. 51-67, 1992.

* cited by examiner

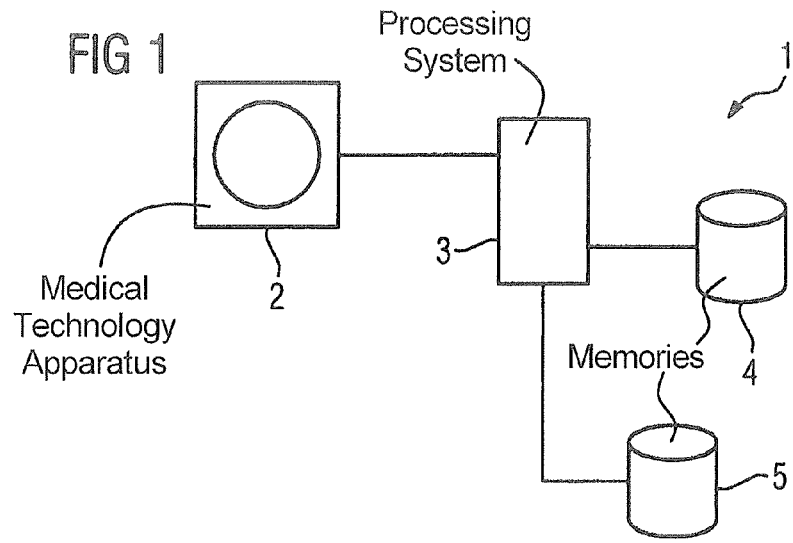
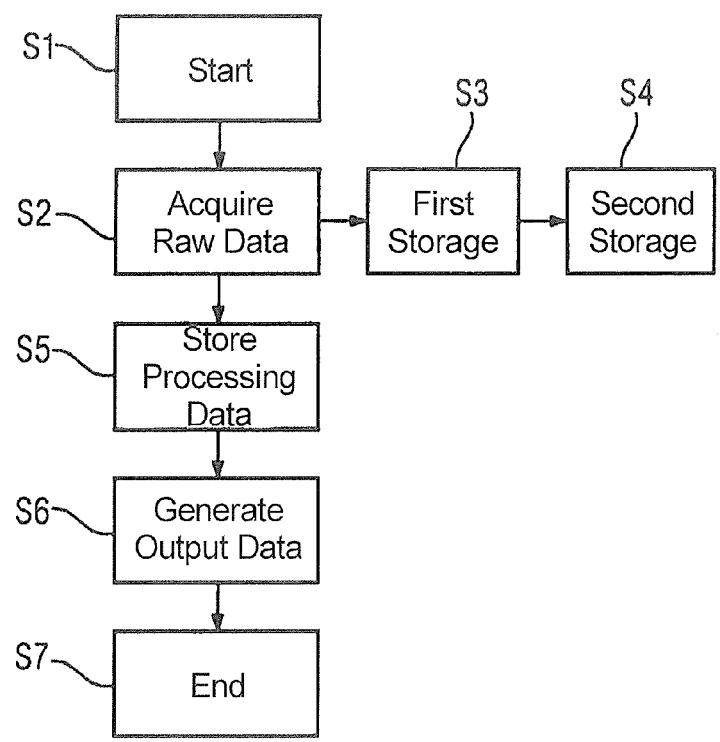

METHOD TO PROCESS MEDICAL IMAGE DATA

BACKGROUND OF THE INVENTION

1. Field of the Invention

The present invention concerns a method to process medical image data, in particular to process data acquired with a magnetic resonance tomography apparatus.

2. Description of the Prior Art

Methods for data acquisition and processing in a magnetic resonance system are known from, for example, DE 10 2009 050 662 A1, DE 10 2009 019 592 A1 and from DE 10 2009 055 122 A1.

The processing of image data—in particular three-dimensional image data acquired, for example, by magnetic resonance methods or x-ray methods, in particular computed tomography—is established in medical engineering, wherein the data sets to be processed have tended to become larger in the course of technological development.

In order to not let data sets that are to be stored (typically that are to be archived in the long term) grow too much, data are frequently stored in a compressed form (not limited to medical engineering). Among others, the ISO/IEC 10918-1 standard—shortened to the JPEG (Joint Photographic Experts Group) standard—is common as a standard for the compression of image data. In principle, a lossless compression (JPEG Lossless Mode) is possible according to the JPEG standard; however, quality losses (for instance in the color space conversion and in the low pass filtering) are normally accepted in favor of a higher compression rate. In medical engineering, the DICOM standard has been established for the storage and exchange of data.

SUMMARY OF THE INVENTION

An object of the invention is to further develop the processing of medical image data relative to the cited prior art, in particular with regard to an efficient use of information.

According to the invention, this object is achieved by a method with the following features.

Immediately compressed raw data are acquired by means of an imaging medical technology apparatus, and the compressed raw data are stored. In addition to the compressed raw data, processing data are stored that are provided to generate output data (image data) from the compressed raw data, wherein the file size of the compressed raw data and the processing data in total is less than the file size of the output data.

The invention proceeds from the fact that, in order to reduce the storage space required for archiving of the data, compressed data are often generated from acquired two-dimensional or three-dimensional raw data according to conventional methods in medical engineering.

However, it has become possible to already reduce the data rate at the acquisition side (i.e. directly in the acquisition of the raw data) with the use of powerful graphics processors (GPU, Graphical Processing Unit), which is different than in conventional methods of data acquisition, compression and storage. Such methods are designated as CS methods ("Compressed Sensing" or "Compressed Sampling") and are described in the following articles, for example:

Romberg J.; Imaging via Compressed Sampling (Introduction to compressive sampling and recovery via convex programming); IEEE Signal Processing Magazine; p. 14 Mar. 2008

Candès E. J., Walkin M. B.; An Introduction to Compressive Sampling (A sensing/sampling paradigm that goes against the common knowledge in data acquisition); IEEE Signal Processing Magazine; p. 21 Mar. 2008

Lustig M., Donoho D., Pauly J. M.; Sparse MRI: The Application of Compressed Sensing for Rapid MR Imaging; Magnetic Resonance in Medicine 58: 1182-1195 (2007)

CS methods combine a compression step with the step of data acquisition in that—insofar as it is possible—only relevant data of the observed subject are collected. This is advantageous in particular in cases in which wide portions of an image to be evaluated have no or little contrast (as this is typical in angiography, for instance). Candès et al. (P. 28, right column, "Applications") go into more detail in this regard. The lower limit of the sampling rate (which lower limit was previously considered to be absolute) which is formulated in the Nyquist-Shannon sampling theorem (a signal must be sampled with at least twice its maximum frequency) does not apply in CS methods. Rather, in CS methods the compression implemented during the sampling provides that a very high image quality is ensured in spite of a distinct undersampling (in comparison to older methods).

A peculiarity of data that were acquired with CS methods is that the acquired input data can have a smaller size than additionally processed, unpacked output data which take the place of typically compressed output data.

Building on this realization, according to the method according to the invention an archiving of output data is abandoned. Instead of this, only input data of the image processing (i.e. acquired data in the CS method) and processing data (with which more comprehensive data that are directly usable for the image evaluation can be generated as needed) are stored.

In preferred alternatives, the known methods of "partial Fourier" or parallel computation such as GRAPPA (Generalized Autocalibration PPA (PPA=Partially Parallel Acquisition)) or SENSE (Sensitive Encoding) are used to compress the data in their acquisition.

The storage of processing data can take place in various advantageous ways, wherein various types of processing data respectively exist.

According to a first concept, the processing data are stored in the form of a loading module. This concept is in particular considered if it can be assumed that the software and hardware platform that is used to acquire, archive and process the image data remains invariant. The loading module is hereby a computation program that is matched to the software and hardware platform that is used.

According to a second concept, the processing data are stored as source code. In comparison to the first concept, only a loose connection (based on a defined standard) to a software and hardware platform is hereby provided. In this case the computation program providing the processing data is stored as source code, complying with simple, precisely specified standards (for example the C++ standard ISO/IEC 14882 from 1998; POSIX: Portable Operating System Interface (DIN/EN/ISO/IEC 9945)). Free basic libraries (for example ATLAS BLAS & LAPACK lib) for compiling and executing on standard architectures are furthermore stored together with the compressed image data present as input data, as well as those basic libraries that are not present elsewhere and are usable at any time for the processing of the compressed data.

According to a modification of the second concept, the processing data are stored as partially translated intermediate code that is not human-readable. This is considered in particular when a specific compiler (gcc for example, possibly with version number) is provided.

According to a third concept, the processing data are stored in the form of a computation program in a platform-independent programming language. For example, JAVA [sic], Python or C# is usable as a programming language. The compatibility across multiple platform generations is hereby ensured, wherein methods for versioning also enable backwards compatibility.

According to a fourth concept, the processing data are stored as generically formulated computation algorithms. This is advantageous in particular when the data should be archived over a very long period of time and independent to the greatest possible extent of the software and hardware platform. A suitable code generator can hereby generate a run-capable source code for the respective platform from an exemplary specification of the computation program (in XML, for example), such that the output data can be synthesized.

According to each of the explained concepts, by displacing a compression step into the data acquisition the invention offers the possibilities to archive raw data in the long term with conservative manipulation with storage capacities, and simultaneous preservation of a high image quality on the basis of image data determined from the raw data.

BRIEF DESCRIPTION OF THE DRAWINGS

FIG. 1 shows an examination device with an imaging medical technology apparatus in a schematic view.

FIG. 2 is a flowchart of an embodiment of a method to process raw data generated by the medical technology apparatus according to FIG. 1.

DESCRIPTION OF THE PREFERRED EMBODIMENTS

An examination device (that is characterized as a whole with the reference character 1) comprises an imaging medical technology apparatus 2, namely a magnetic resonance tomography apparatus with regard to whose principle function the prior art already cited is referenced.

The examination device 1 is designed to directly acquire compressed raw data according to the CS (Compressed Sensing) method and comprises a data processing system 3 which is not necessarily realized as a single apparatus (as it is symbolically represented in FIG. 1). Rather, the data processing system 3 can also be a data processing network. Such a data processing network is in particular usable for a PACS (Picture Archiving and Communication System). The data processing system 3 is connected with a first memory 4 and a second memory 5 (which are shown in FIG. 1 as separate units merely to illustrate the logical structure). While the first memory 4 is used primarily given running data processing processes, the second memory 5 serves for the archiving of data.

The CS methods that can be implemented with the examination device, which are in principle known from the aforementioned articles (Romberg; Candès et al.; Lustig et al.), are nonlinear, iterative methods in which the respective computation method that is used has a specific influence on the output data. In all cases, in a CS method a compression of data takes place at the input side, i.e. immediately in the course of the data acquisition. In contrast to established methods of data compression at the output side—in particular JPEG—there exist in the prior art no standard computation methods for compression methods at the input side. Rather, the computation methods can be tailored to the respective application. This circumstance is allowed for according to the invention in that different concepts of data processing and archiving (that are explained in detail in the preceding) can be realized depending on the requirements. In general, given data acquisition with a CS method the output data can be reproduced identically only with knowledge of the respective computation method and the boundary conditions that were thereby used.

A method of data acquisition, processing and archiving that can be implemented with the examination device 1 is explained in detail in the following as an example using FIG. 2.

The start of the method is identified as a first method step S1. In Step S2, the acquisition of raw data takes place using the CS method by means of the magnetic resonance tomograph 2. Instead of a magnetic resonance tomograph, a computer tomograph or a simpler x-ray apparatus would also be usable as an imaging medical technology apparatus within the examination device 1, for example.

The (at least two-dimensional, typically three-dimensional) compressed raw data that are acquired in Step S2 and compressed in any event during the acquisition are transferred in Step 3 into the first memory 4, which serves as a temporary memory. Insofar as these compressed raw data (i.e. input data) should already be evaluated at this point in time (i.e. before archiving), this optionally takes place in Step S4. Output data—namely directly evaluable image data—are hereby generated from the acquired, compressed raw data using a suitable algorithm, for which processing data depending on the software and hardware platform are used. The total file size of the processing data and the input data is significantly less (for example at least 50% less, in particular at least ⅔ less) than the total size of the output data. The storage of the output data takes place in the first, temporary memory 4.

In no event is an archiving of the output data provided. Rather, the (in comparison to the input data) significantly more comprehensive output data are deleted after their evaluation. In contrast to this, the input data are archived, which takes place in Step S5 via storage in the second memory 5. In addition to the input data, the processing data required to use them (which processing data in particular comprise a computation program) are also stored for the long term in the memory 5. Step S5 is not necessarily implemented after Step S4. Rather, a transfer of data into the memory 5 used for archiving can also be provided immediately after the data acquisition, independently of at which point in time after the data acquisition a first evaluation of the data acquired with the apparatus 2 takes place.

In order to evaluate the compressed data stored in the memory 5 at an arbitrary point in time, the output data (which, as in Step S4 are stored in the temporary memory 4) are generated from these compressed input data in Step S6 using the processing data. If the evaluation of the data has concluded, the output data are erased again and the method concludes with Step S7, wherein the archived input data compressed by means of a CS method remain usable at any time.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to process medical raw data, comprising:
   operating a medical imaging apparatus to acquire medical data in a compressively sampled data acquisition procedure wherein said medical data are undersampled at a sampling rate that does not obey Shannon's Theorem, thereby producing compressively sampled raw data, and providing said compressively sampled raw data to a processor;

in said processor, controlling storage of the compressively sampled raw data in a memory;

in said processor, in addition to the compressively sampled raw data, controlling storage of processing data configured to operate on the compressively sampled raw data to generate output data, in an output data file, with the compressively sampled raw data and the processing data being stored in a file in said memory having a file size that is less than a file size of said output data file; and making said output data file available at an output of said processor in electronic form.

2. A method as claimed in claim 1 comprising storing said processing data configured as a loading module.

3. A method as claimed in claim 1 comprising storing said processing data as source code.

4. A method as claimed in claim 1 comprising storing said processing data as partially translated intermediate code.

5. A method as claimed in claim 1 comprising storing said processing data as a computation program in a platform-independent programming language.

6. A method as claimed in claim 1 comprising storing said processing data as generically formulated computation algorithms.

7. A medical examination apparatus comprising:

a medical imaging apparatus configured to acquire medical data in a compressively sampled data acquisition procedure wherein said medical data are undersampled at a sampling rate that does not obey Shannon's Theorem, thereby producing compressively sampled raw data;

a memory in communication with said medical imaging apparatus, in which the compressively sampled raw data are stored;

a computerized processor configured to control storage of said compressively sampled raw data in said memory, and to control storage of processing data in said memory together with said compressively sampled raw data;

said computerized processor being configured to operate on said compressively sampled raw data to generate output data, in an output data file, and to control said storage of said compressively sampled raw data and said processing data in said memory so as to store said compressively sampled raw data and said processing data in a file in said memory having a file size that is less than a file size of said output data file; and said computerized processor being configured to make said output file available in electronic form at an output of said computerized processor.

* * * * *